US009290756B2

(12) United States Patent  
Ross et al.

(10) Patent No.: US 9,290,756 B2  
(45) Date of Patent: Mar. 22, 2016

(54) APPARATUS AND METHODS FOR HIGH THROUGHPUT NETWORK ELECTROPHYSIOLOGY AND CELLULAR ANALYSIS

(75) Inventors: James Ross, Decatur, GA (US); Edgar A. Brown, Decatur, GA (US); Swaminathan Rajaraman, Atlanta, GA (US); Mark G. Allen, Atlanta, GA (US); Bruce Wheeler, Gainesville, FL (US)

(73) Assignees: The Board of Trustees of the University of Illinois, Urbana, IL (US); Georgia Tech Research Corporation, Atlanta, GA (US)

( * ) Notice: Subject to any disclaimer, the term of this patent is extended or adjusted under 35 U.S.C. 154(b) by 1333 days.

(21) Appl. No.: 12/615,778

(22) Filed: Nov. 10, 2009

(65) Prior Publication Data

US 2010/0120626 A1    May 13, 2010

Related U.S. Application Data

(60) Provisional application No. 61/113,103, filed on Nov. 10, 2008.

(51) Int. Cl.
*G01N 33/487*  (2006.01)
*C12N 13/00*   (2006.01)
(Continued)

(52) U.S. Cl.
CPC ............. *C12N 13/00* (2013.01); *C12M 1/42* (2013.01); *G01N 33/4836* (2013.01); *G01N 33/48728* (2013.01); *B32B 2535/00* (2013.01); *G01N 33/48735* (2013.01); *Y10T 156/10* (2015.01)

(58) Field of Classification Search
CPC .............. C12N 13/00; G01N 33/4836; G01N 33/48728; G01N 33/48735; C12M 1/42; B32B 2535/00

USPC ......................................................... 506/7
See application file for complete search history.

(56) References Cited

U.S. PATENT DOCUMENTS 4,806,432 A * 2/1989 Eguchi et al. ................. 428/457  
5,965,452 A   10/1999 Kovacs et al.  
(Continued)

OTHER PUBLICATIONS

Oka et al., Journal of Neuroscience Methods, 1999, 93:61-67.*  
(Continued)

*Primary Examiner* — Jeremy C Flinders  
(74) *Attorney, Agent, or Firm* — Meunier Carlin & Curfman LLC

(57) ABSTRACT

Provided herein are apparatus and methods relating to the development of instrumentation for high throughput network electrophysiology and cellular analysis. More specifically, provided herein are multiwell microelectrode arrays (MEAs) and methods for the development of such an apparatus in an inexpensive fashion with a flexible, ANSI/SBS-compliant (American National Standards Institute/Society for Biomolecular Screening) format. Microelectrode arrays are a grid of tightly spaced microelectrodes useful for stimulating and sensing electrically active cells, networks and tissue. The techniques described herein relate to the use of microfabrication in combination with certain large-area processes that have been employed to achieve multiwell MEAs in ANSI/SBS-compliant culture well formats, which are also transparent for inverted/backside microscopy compatibility. These multiwell MEAs can be used to investigate two and three-dimensional networks of electrically active cells and tissue such as cardiac, neural, and muscular in a high throughput fashion. Also being ANSI/SBS-compliant, they are compatible with machinery and robotics developed for the pharmaceutical industry for drug screening applications.

44 Claims, 10 Drawing Sheets

(51) Int. Cl.
*C12M 1/42* (2006.01)
*G01N 33/483* (2006.01)

(56) References Cited

U.S. PATENT DOCUMENTS

| | | | |
|---|---|---|---|
| 6,132,683 A * | 10/2000 | Sugihara et al. | 422/82.01 |
| 6,352,853 B1 | 3/2002 | King et al. | |
| 6,969,449 B2 | 11/2005 | Maher et al. | |
| 7,192,752 B2 | 3/2007 | Xu et al. | |
| 7,267,751 B2 | 9/2007 | Gelbart | |
| 2005/0006234 A1 | 1/2005 | Hassibi | |
| 2006/0018833 A1 * | 1/2006 | Murphy et al. | 424/9.2 |
| 2006/0057771 A1 * | 3/2006 | Kovacs et al. | 438/106 |
| 2007/0178579 A1 | 8/2007 | Ross et al. | |

OTHER PUBLICATIONS

French et al., Photovoltaic Specialists Conference (PVSC), 2009 34th IEEE, 2009, pp. 394-399.*
ANSI_SLAS_Jan. 2004_FootprintDimensions.*
ANSI_SLAS_Feb. 2004_HeightDimensions.*
Morin et al. (Biosensors and Bioelectronics, 2006, vol. 21, pp. 1093-1100).*
Blum et al., 2007, "An integrated system for simultaneous, multichannel neuronal stimulation and recording," IEEE Trans. On Circuits and Systems, vol. 54(12):2608-2618.
Brown et al., 2008, "Stimulation and recording of neural tissue: Closing the loop on the artifact," IEEE , Invited Paper, Georgia Institute of Technology, pp. 356-359.
Brown et al., 2008, "Stimulus-Artifact elimination in a multi-electrode system," IEEE Trans. on Biomed. Circuits and Systems, vol. 2(1):10:21.
Cullen et al., 2007, "Microfluidic engineered high cell density three-dimensional neural cultures," J of Neural Engineering, 4:159-172.
Dunlap et al., 2008, "High-throughput electrophysiology: an emerging paradigm for ion-channel screening and physiology," Nature Reviews Drug Discovery.
Giovangrandi et al., 2006, "Low-cost microelectrode array with integrated heater for extracellular recording of cardiomyocyte cultures using commercial flexible printed circuit technology," Sensors and Actuators B, 113:545-554.
Joung et al., 2008, "Inter-substrate microstructure formation by electroplating bonding technology," J of Micromechanics and Microengineering, vol. 18:1-12.
Lorenz et al., 1998, "High-aspect-ratio, ultrathick, negative-tone near-UV photoresist and its applications for MEMS," Sensors and Actuators A, vol. 64:33-39.
Rajaraman et al. 2007, "Three-dimensional metal transfer micromolded microelectrode arrays for in-vitro brain slice recordings," IEEE Transducers Conf., Lyon, France (Jun. 10-14, 2007): 1251-1254.
Rajaraman et al., 2007, "Microfabrication technologies for a couples three-dimensional microelectrode, microlluidic array," J of Micromechanics and Microengineering, vol. 17:163-171.
Rennaker et al., 2005, "An economical multi-channel cortical electrode array for extended periods of recording during behavior," J of Neuroscience Methods, vol. 142:97-105.
Ross et al., 2004, "Multielectrode impedance tuning: Reducing noise and improving stimulation efficacy," Proceedings of 26th Annual Intl Conf of IEEE EMBS, Sep. 1-5, pp. 4115-4117.
Standards for Microplates, American National Standards Institute/ Society for Biomolecular Sciences, 2004.
Wise, 2005, "Silicon Microsystems for neuroscience and neural prostheses," IEEE Engineering in Medicine and Biology Magazine, pp. 22-29.

* cited by examiner a. Fabricate rigid PCB with copper patterns and central hole for optical view port b. Render PET compatible with PCB lamination c. Laminate PET on PCB d. Post-process for microelectrodes

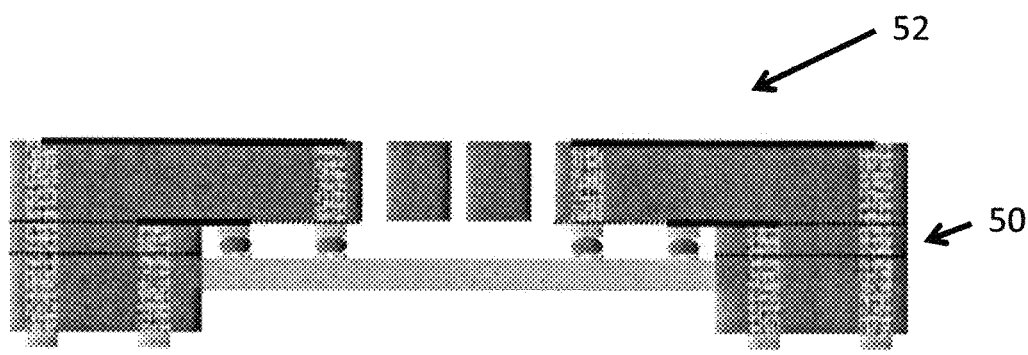
Figure 5A
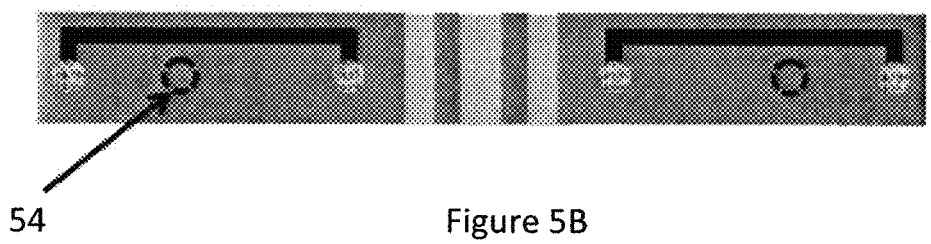
Figure 5B
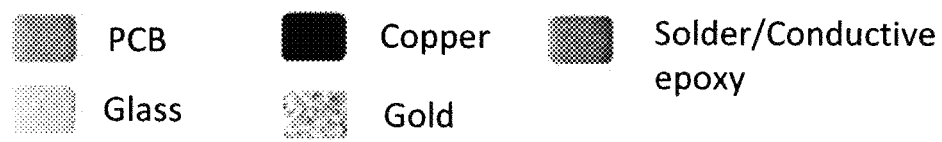

ically low-throughput manner. For example, patch clamp systems, have an extensive history of use in identifying specific perturbations in electrophysiological function; however, they are also well known for their extremely low throughput (<10 cells/day). On the other hand, microelectrode array (MEA) systems, which have concurrent access to both single-cell and network-level activity, are higher-throughput and less technique-dependent; however, due to their high cost and limited sample capacity (typically <5 samples/experiment), they are still, functionally, low throughput. Currently, MEAs are expensive and are typically offered in units with only one culture well (such that only one tissue sample/cellular network at a time can be studied). The use of only one culture-well severely limits the throughput with which MEAs can be used to interface and investigate electrically active cellular networks.

APPARATUS AND METHODS FOR HIGH THROUGHPUT NETWORK ELECTROPHYSIOLOGY AND CELLULAR ANALYSIS

This application claims the benefit of U.S. Provisional Application No. 61/113,103, filed Nov. 10, 2008, the entire contents of which are incorporated herein by reference.

STATEMENT REGARDING FEDERALLY SPONSORED RESEARCH OR DEVELOPMENT

This invention was made with Government support under agreement number 1 R01 EB00786-01, awarded by the National Institutes of Health. The Government has certain rights in the invention.

BACKGROUND

Electrophysiological-based assays are used in a variety of applications, which include the detection of toxicants, drug screening, illuminating the mechanism of toxicity, neuronal injury, epilepsy studies and biosensing. Most systems used for such assays produce information in a relatively low-throughput manner. For example, patch clamp systems, have an extensive history of use in identifying specific perturbations in electrophysiological function; however, they are also well known for their extremely low throughput (<10 cells/day). On the other hand, microelectrode array (MEA) systems, which have concurrent access to both single-cell and network-level activity, are higher-throughput and less technique-dependent; however, due to their high cost and limited sample capacity (typically <5 samples/experiment), they are still, functionally, low throughput. Currently, MEAs are expensive and are typically offered in units with only one culture well (such that only one tissue sample/cellular network at a time can be studied). The use of only one culture-well severely limits the throughput with which MEAs can be used to interface and investigate electrically active cellular networks.

In contrast, multiwell culture plates and plate readers are commonly used instruments in the pharmaceutical industry and are extensively used for high throughput in-vitro assays, such as screening compounds or toxicants. However, apart from enabling imaging, such transparent plates have no other function than to act as supporting structures for cell cultures and media, which eliminates the possibility of using multiwell plates for electrophysiological investigations. If electrodes could be integrated into to these transparent plates, high throughput applications like network electrophysiology can be carried out in a standard format. Integrating microelectrodes into a standard format would additionally enable compatibility with machinery in place for analysis of multiwell plates like microscopy and cell counting.

King et al. and Maher et al. disclose electrode arrays integrated with multiwell plates but the electrodes used are macro-sized (4 mm wide, 1 cm long and 0.2 mm thick in the case of Maher et al.) stainless steel plates. King et al. discloses an electroporation application to introduce molecules into lipid vesicles of cell membranes and Maher et al. report stimulation of cells in-vitro for studying transmembrane potentials recorded with optical measurement techniques. These disclosures by King et al. and Maher et al., introduce electrodes into multiwell formats, but the large size of the integrated electrodes eliminate the possibility for any cell based assays that address both single and network level cellular activity. Thus, micro-scale electrodes are required for such an investigation and the invention provided herein addresses the novel integration of microelectrodes into multiwell plates, such as a multiwell culture plate, with a transparent substrate in an ANSI/SBS (American National Standards Institute/Society for Biomolecular Sciences, "Standards for Microplates", 2004) compliant format. However, the integration of micro-scale electrodes or MEAs into transparent, large area multiwell plates presents significant manufacturing challenges.

To-date, MEAs have been fabricated in both two- and three-dimensional conformations on a myriad of different substrates including flexible materials, such as poly dimethyl siloxane (PDMS), and rigid substrates, like silicon and glass. Regardless of the application or material, many of these MEAs share one significant drawback, expensive manufacturing costs. This expense is derived primarily from the packaging and assembly of the device, which is required to connect micron-sized electrodes for cellular interfacing to millimeter-sized sockets and pads for electrical processing. Such differences in scale introduce intermediate, often manual, processing steps that significantly reduce the manufacturability of MEAs. Additionally none of these known processes is truly standard (eg. Complimentary Metal Oxide Semiconductor or CMOS process for computer chips) resulting in high processing costs.

SUMMARY OF THE INVENTION

Provided herein are microelectrode array devices, methods for their use and methods for their manufacture.

In addition to enabling high-throughput extracellular electrophysiological investigations of electrically active tissues and cultures, the approaches taken in connection with this invention address the interconnection of macro-sized sockets and pads for electrical interfacing to micro-sized electrodes for cellular interfacing utilizing two different techniques: one is a novel post-processing approach on a modified, commercially available printed circuit boards (PCBs) that enables majority of the device being built by a low-cost, large area (eg, a surface area of about 3 inches by 3 inches, or greater) process on a transparent substrate; second is a flip-chip bonding approach of a separately fabricated glass die with microelectrodes with an innovatively designed printed circuit board for the macro-sized electrical connections. Both these approaches have been designed to fit into a standard multiwell plate (ANSI/SBS 2004 standards) that measure 127.76±0.25 mm in length and 85.48±0.25 mm in width. This multiwell plate can house 6, 12, 24, 48, 96, 384, and 768 culture wells depending on the application. Multiwell plates are an integral part of the biological and pharmaceutical industries, with standardized overall dimensions covered by ANSI/SBS 2004 standards. None of these standards cover the use of electrodes.

In exemplary embodiments, the electrodes are 500 μm or smaller in diameter with the space between the electrodes also being 1 mm or smaller. In addition to transparency, this small size area requires a specialized manufacturing process. Additionally, an individual multiwell MEA plate may contain hundreds to thousands of electrodes.

In exemplary embodiments, the manufacturing process for multiwell microelectrode array includes post-processing or microfabrication directly onto the PCB (or package) or an integrated circuit (IC) packaging approach that combines microfabricated die with a PCB. Either technique makes use of the PCB industry, which employs standard large-area processes to achieve precise, high-density metal traces, sockets, vias and pads (minimum PCB features sizes are typically around 125 µm). Additionally, even higher electrode densities can be achieved by augmenting or post processing the PCB process with microelectromechanical (MEMS) based processing (minimum MEMS features sizes may be less than 1 µm, approximately two orders of magnitude below PCB processes). This high-density microelectrode fabrication is enabled by the small features sizes of MEMS processes and by micro-scale multilayer electrode wiring (existing MEAs use a single wiring layer). In the composite device (PCB+ MEMS processing), commercial high-density electrical connectors can be used to connect to thousands of electrodes in the back/bottom layer of the multiwell MEA. Existing MEAs, due to manufacturing limitations, tend to use top-layer connectors; which reduces the number of interconnects that can be used and increases the footprint of the device to accommodate the required interconnects. The use of commercial PCB technology allows the addition of standard integrated circuits (ICs) and other components to provide improved functionality to the MEAs. These additional components may include the introduction of memory, heater, and sensor elements directly onto the multiwell MEA substrate.

BRIEF DESCRIPTION OF THE DRAWINGS

FIGS. 5A-B illustrate an exemplary packaging approach to a multiwell MEA with side and top views, respectively.

DETAILED DESCRIPTION

Figure 1:
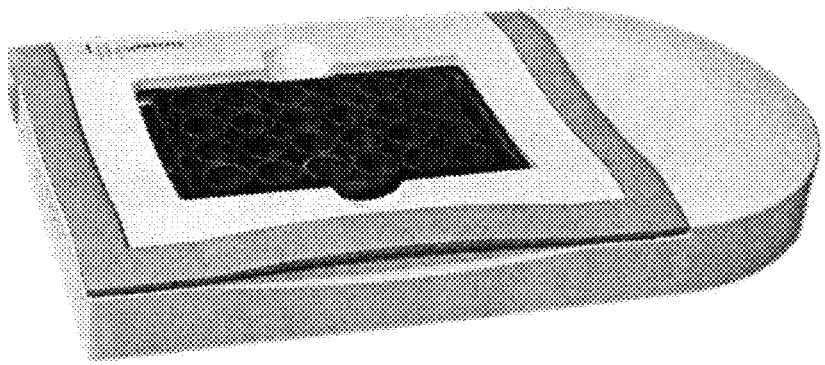
FIG. 1 illustrates an exemplary embodiment of a multiwell MEA in an ANSI/SBS-compliant format.
Figure 1:
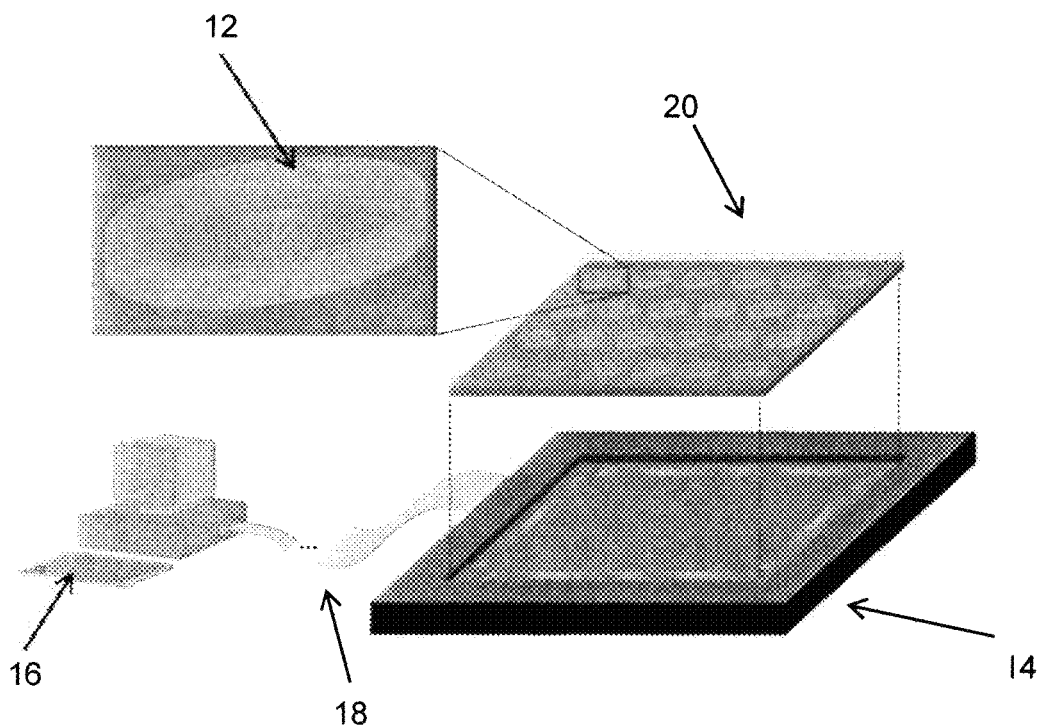

FIG. 1 illustrates an exemplary embodiment of a multiwell MEA in an ANSI/SBS-compliant format. The multiwell electrode interfaces with electronics to which it is attached to through bottom side contacts. The electronics amplify and process the raw data obtained from cellular cultures in the various wells and the data is reflected in a computer for data analysis and manipulation.

FIG. 1 illustrates an exemplary MEA system 10 that has been designed to interface with a physical system such as a tissue specimen or a network of cells in a multiwell format, i.e. several wells 12 of electrodes (6, 12, 24, 48, 96, 384, and 768 with a total of 768 electrodes). This physical system is in direct contact with the microelectrodes. The multiwell microelectrodes 20 plug into a signal processing and data management system 14 which collects and analyzes the data that is generated from the cells. The combination of the cells, microelectrodes and entire system connects to a computer 16 via a data cable 18 for real time software analysis and recording. At the top of FIG. 1 is a constructed multiwell MEA system 8.

Figure 2A:
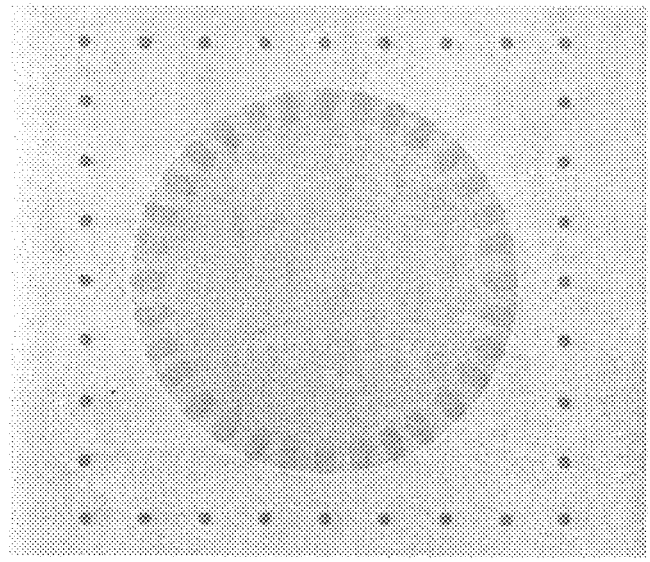
FIGS. 2A-B and 2C-D illustrate top and side views, respectively, of post-processing on a printed circuit board.
Figure 2B:
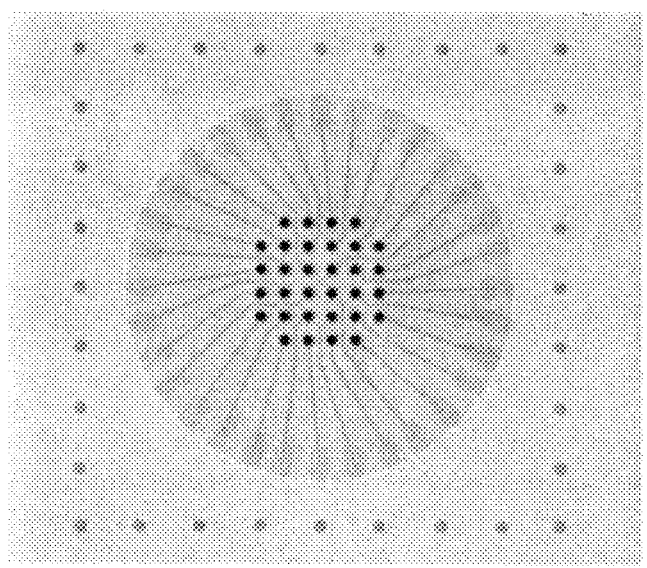
Figure 2C:
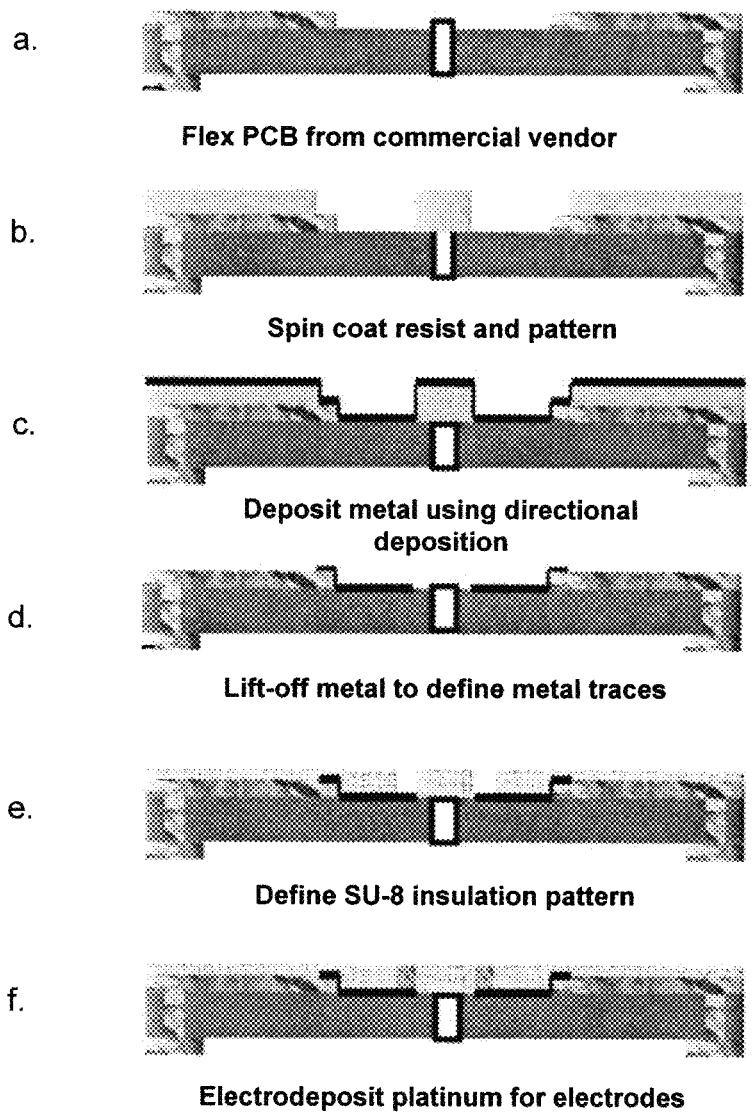
Figure 2D:
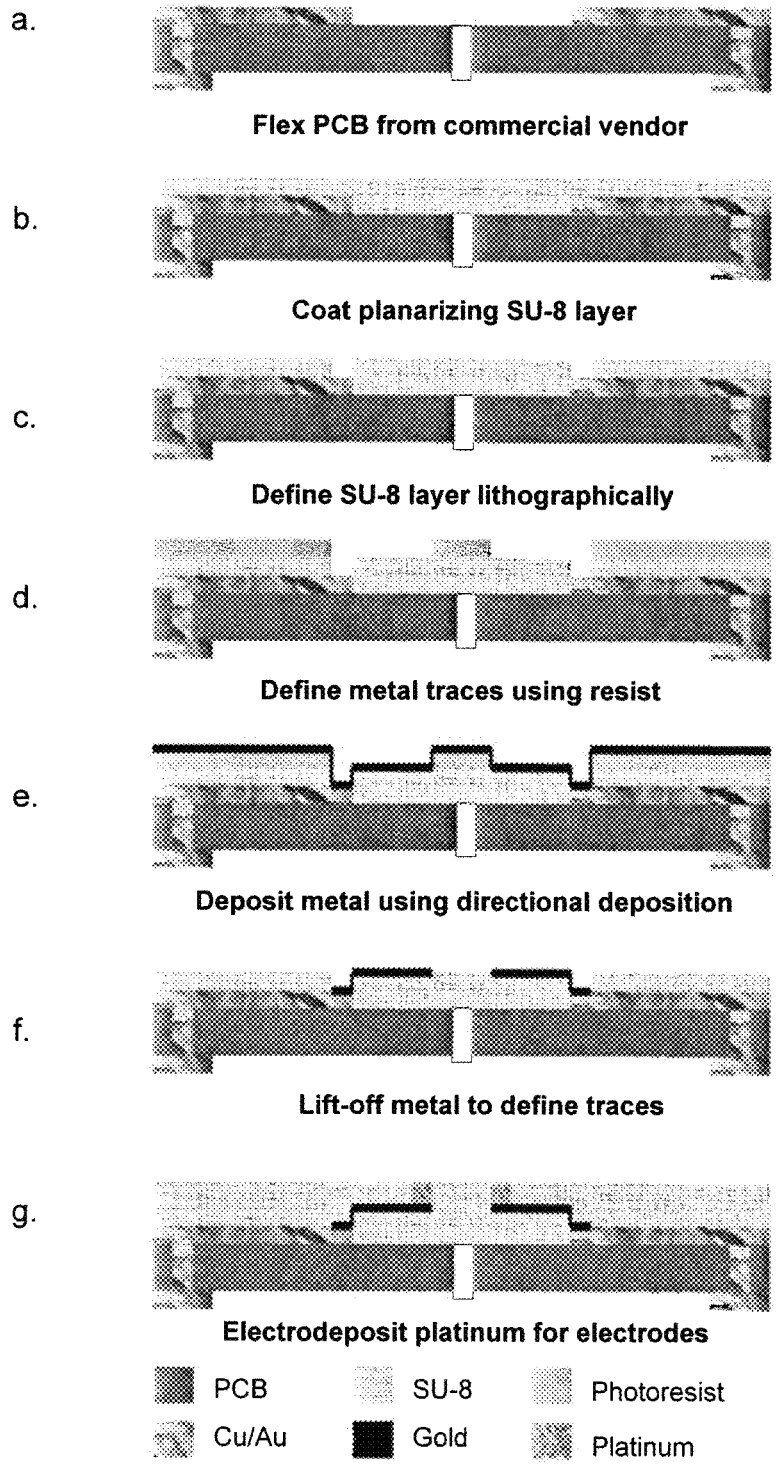

FIGS. 2A-B and 2C-D illustrate top and side views, respectively, of post-processing on a printed circuit board. FIGS. 2A and 2B illustrate microfabrication of the multiwell MEA using a combination of a large area process like PCBs and post processing using microfabrication or MEMS techniques—top views of a PCB (obtained from a commercial vendor) and a single well of electrodes after post processing. FIGS. 2C and 2D illustrate side views for the fabrication strategies for a multiwell MEA with a large area process like PCB in combination with microfabrication techniques.

FIG. 2A depicts the components of a planar MEA. The active part of a planar MEA comprises three components: (1) the electrodes or the active sites, (2) the topmost insulating layer, and (3) the micro-scale metal wiring traces. Regardless of the manufacturing strategy, the microfabrication process must account for all these three components. For the development of multiwell MEA devices, platinum black can be used for the electrodes, SU-8 or silicon dioxide ($SiO_2$) for the insulation layer, and gold for the wiring traces. The platinum black electrodes can be formed using a closed-loop electroplating process, which will produce robust electrodes with precisely matched electrical properties. The negative tone epoxy SU-8, which acts as an insulating material, has several attractive properties such as chemical stability, photolithographic definition, thermal stability and coating uniformity. It has been used as an insulation layer in commercially available MEAs from Ayanda Biosystems. Additionally, SU-8 has the added benefit of planarizing the relatively rough surfaces on PCBs substrates or flex-rigid circuits. SU-8 is an ideal material to act as an insulation layer for a polymer-substrate multiwell MEAs, which have low temperature processing requirement, though it can be used with glass or silicon substrate materials as well. Silicon dioxide is a traditional insulation material that is used in combination with rigid substrates like glass. The advantages of silicon dioxide include well characterized microfabrication techniques, low dielectric constant and pin-hole free coatings even in a nanometer scale. Although SU-8 has been used with both polymer and glass substrates for multiwell MEA fabrication, $SiO_2$ has been used exclusively with glass substrates (FIGS. 5 and 6).

With these materials in mind, provided herein are fabrication processes and strategies for a post-processing of PCB that include the minimum number of steps necessary to achieve the desired objectives, such as transparency.

FIG. 2C depicts the side view of this fabrication approach. The MEA traces and recording sites can be defined using a relatively thick layer of negative resist (which will also account for the planarization of the metal on the flex circuit) and UV lithography. A biocompatible metal stack (titanium for adhesion and gold for the metal traces) can be deposited using standard metal deposition techniques and the metal will be lifted off to define the finer metal lines. In order to passivate the MEA and define the recording sites (electrodes), a thin layer of SU-8 is coated and the material is photo patterned. SU-8 is photopatterned to define the final insulation pattern. No other processing on top of this is necessary to define the insulation layer. This processing step may be followed by electrodeposition of platinum in order to reduce the impedance of the recording sites. The approach listed here has the advantage of a very simple post-processing strategy (2 mask process) to achieve a functional MEA.

Surface planarization (for microfabrication) on non-standard substrates may require a slightly modified approach to the process described above. One such modified approach is illustrated in FIG. 2D. SU-8 is an excellent material for surface planarization. Spin coating a layer of SU-8 on relatively rough surface results in the reduction of surface non-uniformities. This may be used as an additional step in the beginning of the above processes to address potential problems in direct processing on PCBs. The rest of the process is same as the fabrication techniques detailed above. The additional complexity (involving one more mask) will not add significant time to the process development of multiwell microelectrode arrays. Additionally, potential cytocompatibility problems due to insufficient PCB encapsulation are improved by the addition of an extra layer of SU-8.

Figure 3:
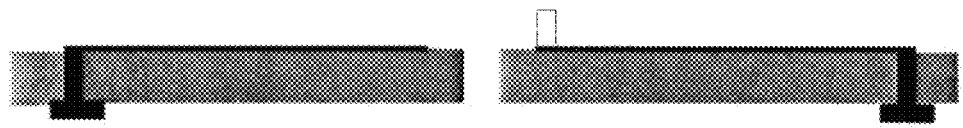
FIG. 3 illustrates a technique to enable the successful lamination with a transparent polymer, which further enables the use of inverted microscopy.
Figure 3:
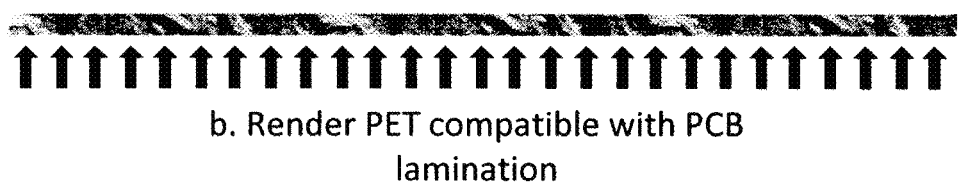
Figure 3:
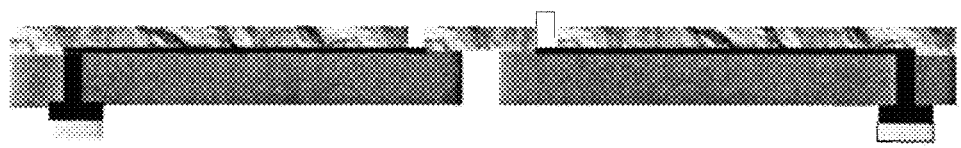
Figure 3:
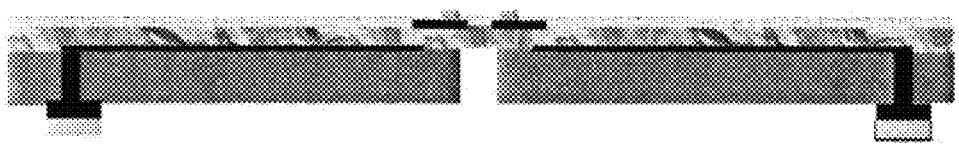
Figure 3:

FIG. 3 depicts a lamination technique for transparent polymer lamination on PCBs that is compatible with standard adhesives used in the industry. Acrylic-based adhesives are used to laminate Kapton onto a printed circuit board for what are called "flex-rigid" or "rigid-flex" circuits since the Kapton layer adds flexibility to what is a rigid substrate. The most common applications for flex-rigid circuits are in the fields of aerospace, military and biomedical. It offers increased reliability and reduced weight for the former two markets while offering the ability to bend and fold in tight places for biomedical applications like implants. Kapton or polyimide is a suitable polymer for these circuits due to its mechanical stiffness, and compatibility with processes for drilling and metallization. Polyethylene Terephthalate (PET) is a transparent polymer (light transmittance of 93% for 3 mil thickness; source DuPont Teijin Films) that could be utilized as an alternate to Kapton utilizing an added step (such as employing an adhesive or a mechanical operation as known to one skilled in the art) to render it compatible with standard PCB processing. The temperature of the lamination process is lowered to accommodate the low temperature requirement of PET but the time of the process is increased to ensure the reflow of this thermally set acrylic adhesive. This reflow ensures that the adhesive remains intact for any future processing. This process has been demonstrated successfully on large area substrates (eg, 12 inches by 18 inches). Several flex rigid circuits with the multiwell format can be fabricated on a single panel PCB making this process batch fabrication compatible. This batch fabrication results in lowering the cost of the PCB process with the primary cost shifting to the post processing, which is low to begin with since there are only two layers to creating the MEA.

Figure 4A:
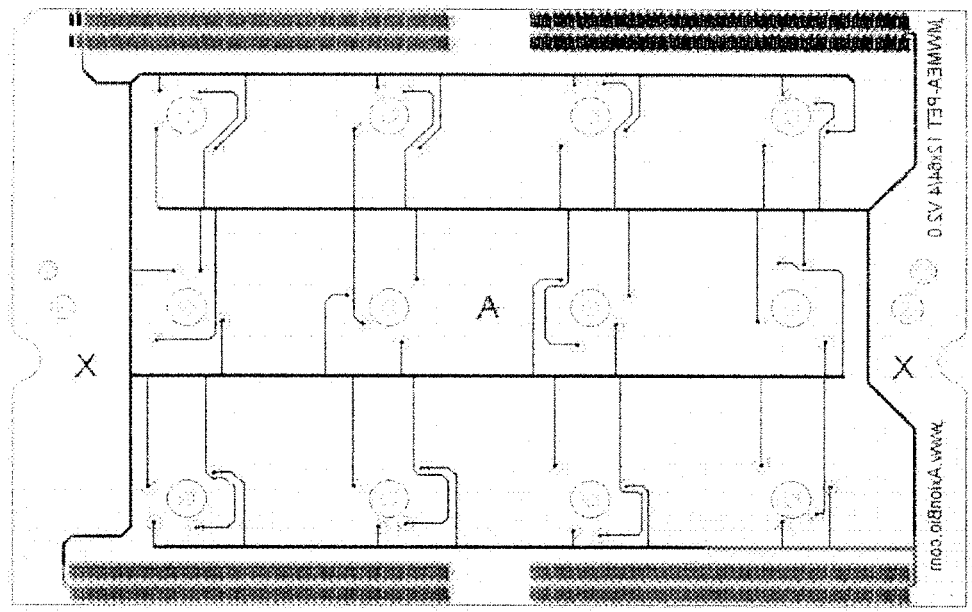
FIGS. 4A-B illustrate an exemplary design of a package/substrate in a multiwell format in a package design layout and microelectromechanical systems (MEMS) post processing layout, respectively.
Figure 4B:
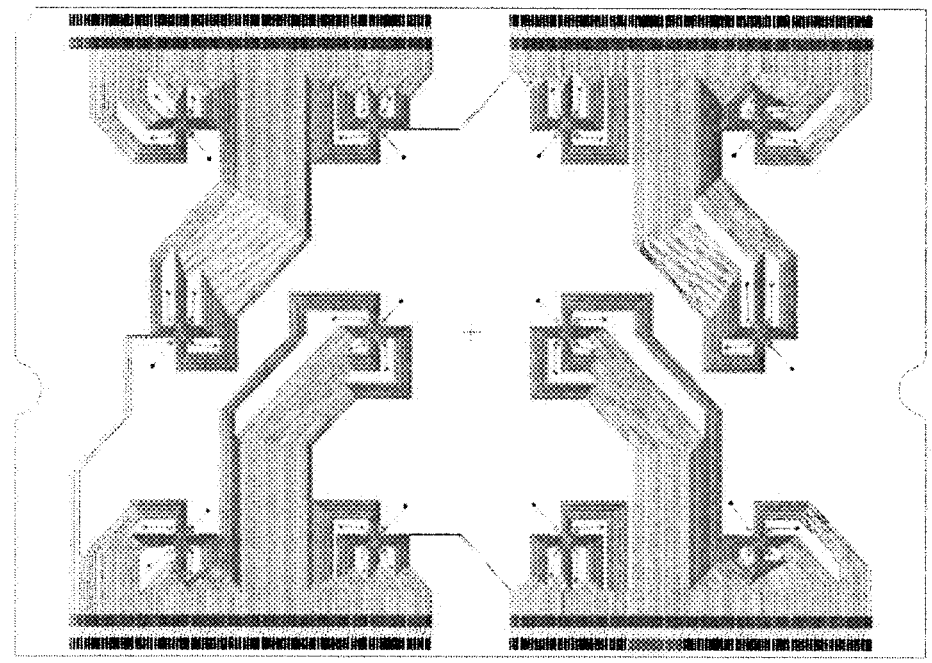

Referring now to FIGS. 4A and 4B, design layouts for the PCB, FIG. 4A, and MEMS post processing, FIG. 4B, for a 12 well multiwell MEA are illustrated. These designs can be rapidly modified to accommodate different well configurations. The circular configurations on the PCB design define holes in the FR-4 substrate that allow for bottomside transparency. Rapid design changes allow for the modification of the MEMS post processing masks, so that other well designs with electrodes can be achieved like 24, 48 and 96 well counts.

FIG. 4A depicts the layout for the PCB (top side) and the masks for post processing to create the multiwell MEAs using the fabrication process described in FIGS. 2A-D. A major advantage is the flexibility of the design and fabrication processes. Specifically, design changes can be implemented rather quickly once the fabrication process has been established. A design iteration only requires two different layouts (PCB layout and MEA mask layout for two layer fabrication), and, by changing these two layouts, a wide variety of electrode counts can be fabricated. Additionally the well locations can be made ANSI/SBS-compliant by incorporating the well locations from standard documents into the designs. Thus, a change from 1×768 (one well with 768 electrodes) to 96×8 (96 wells with 8 electrodes each) or any combination in between can be constructed with little difficulty. The processes also lend to flexibility in terms of changes in electrode densities and geometries with changes only to the MEA mask layout. Furthermore, since the processes are primarily based on custom PCB/flex circuit fabrication, the integration of heaters, sensors, memory chips, and fluidic valve controls to the multi-well MEA itself can be easily accomplished, thus providing additional functionality to the final product.

FIGS. 5A and 5B illustrate the concept of a packaging or flip-chip approach to a multiwell MEA with side and top views, respectively. The multilayer PCB and the glass die can be fabricated separately using batch fabrication techniques and coupled together to complete the device in an ANSI/SBS compliant format. FIG. 5A depicts a side view of the flip chip approach to multiwell MEAs. In this schematic, the two components of the multiwell MEA are depicted: a recessed three layer printed circuit board (standard rigid PCB) 50; and a microfabricated glass chip that has metal traces defined and insulation coated 52. The two components are connected together using a conductive epoxy or solder layer that is screen printed on the glass substrate. The completed device is in an ANSI/SBS-compliant culture well format thereby enabling easy design changes from a 1×768 electrode format (single well) to a 96×8 electrode format (up to 96 wells). The glass substrate is fabricated in two steps: metal interconnection patterns are defined utilizing a standard metal lift-off process; an insulation process which may include either an SU-8 layer defined using photolithography or an $SiO_2$ layer defined using a photolithography step followed by an etch process. The rigid PCB is fabricated using a three-layer process with a bottom layer for connecting the electrodes to the multiwell electronics and two layers on top to accommodate the routing of all 768 electrodes. FIG. 5B depicts a top view of the flip chip approach to multiwell MEAs.

Figure 6A:
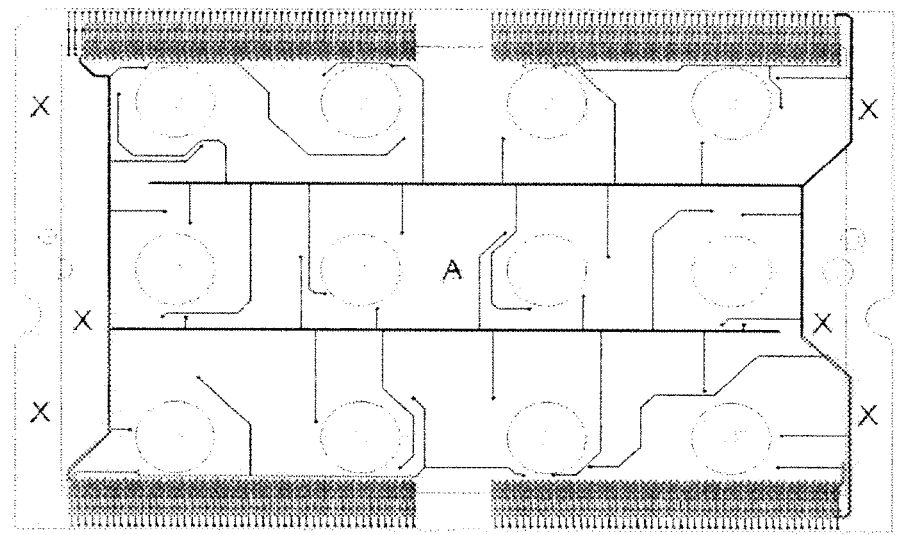
FIGS. 6A-B illustrate an exemplary design of the PCB and glass substrate with top views of the layout for the PCB and the glass substrate used in the packaging process, respectively.
Figure 6B:
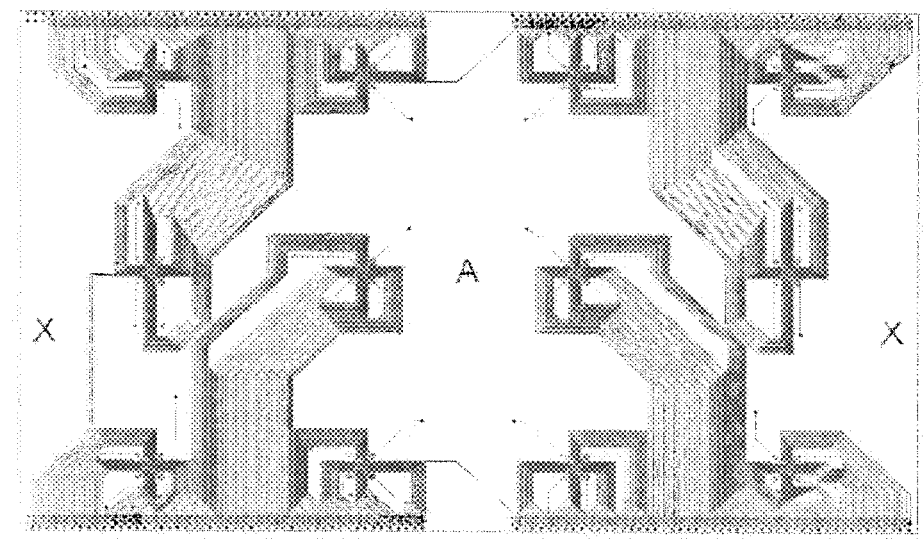

FIGS. 6A and 6B illustrate exemplary design of the PCB and glass substrate with top views of the layout for the PCB and the glass substrate, respectively, used in the flip chip process. These designs can be rapidly modified to accommodate different well configurations. The circular configurations on the PCB design define holes in the FR-4 substrate that allow for bottomside transparency. Rapid design changes allow for the modification of the MEMS post processing masks, so that other well designs with electrodes can be achieved, such as 24, 48 and 96 well counts.

FIGS. 6A and 6B illustrate a sample routing scheme for 768 electrodes in a 12-well format (each well has 64 electrodes). Both the PCB design, FIG. 6A, and the glass plate design, FIG. 6B, are shown. The interconnection between the two substrates is achieved using metal pads defined at two of the corners of both the substrates. Screen printing of a conductive material like conductive epoxy or solder is carried out utilizing standard stencil printing techniques. The glass substrate and the PCB are brought assembled together using a flip chip bonder and the entire assembly is cured to finish the flip chip process to achieve a multiwell MEA in an ANSI/SBS compliant format.

Figure 7A:
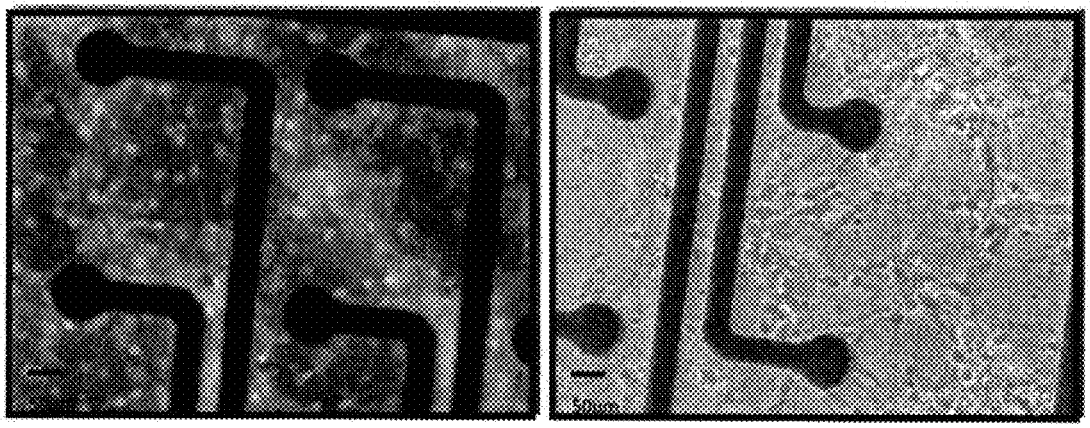
FIGS. 7A-B illustrate optical microscopy images of neuronal cultures grown on the MEAs at 21 and 28 days in-vitro, respectively.
Figure 7B:
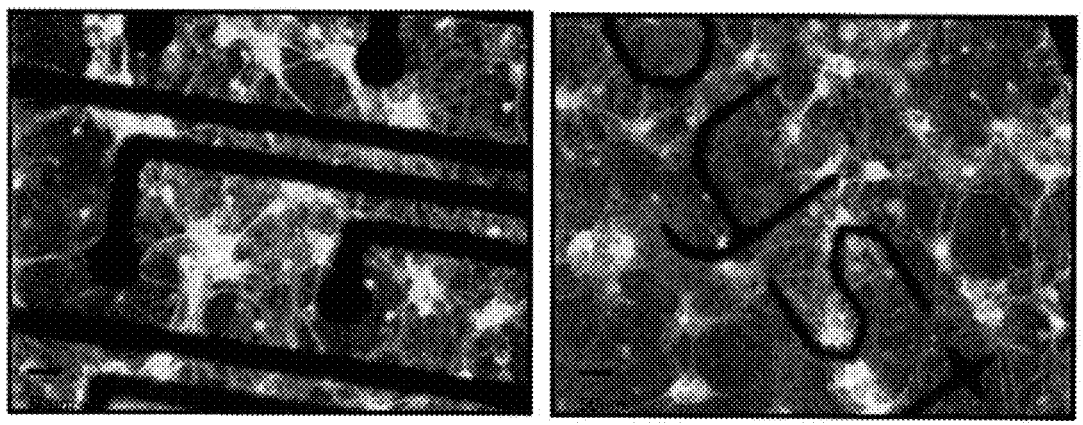

FIGS. 7A and 7B are optical microscopy images of neuronal cultures grown on the MEAs at 21 days, FIG. 7A, and 28 days, FIG. 7B, in-vitro. FIGS. 7A-B depict optical microscopy images of neuronal cells from E18 cortices of rat brains cultured on a single well of the MEA devices. E18 cortices are harvested from rat brains and cells from these cortices are plated on the MEA as described in the Examples section. These devices were placed in incubators and observed after 24 hours of plating cells, at 7 days, 21 and 28 days in-vitro. The observations were carried out utilizing inverted microscopy techniques. Observations were made for neurite outgrowth and general health of the cells. At 28 days in-vitro, a live/dead assay was performed in accordance with the protocols developed by Cullen et al. to access the viability of cells in the culture dish. Images captured from this assay are also shown in FIG. 7A-B. In a multiwell embodiment of the same device, such data will be collected from all the wells simultaneously. The multiwell MEAs will ensure similar experimental conditions for such assays unlike the single well counterparts where these experiments have to be performed one at a time. This will enable a much higher throughput for applications like drug screening.

Figure 8A:
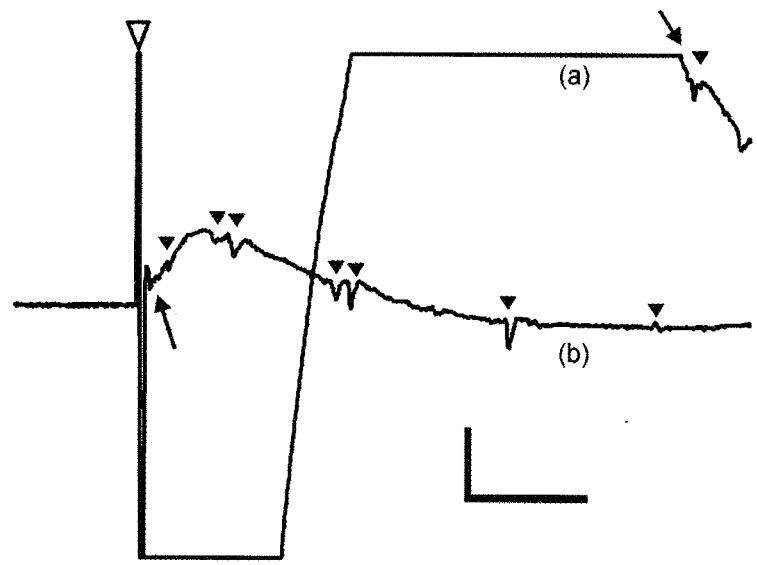
FIGS. 8A-B illustrate evoked electrophysiological data produced from microelectrodes within an individual culture well.
Figure 8B:
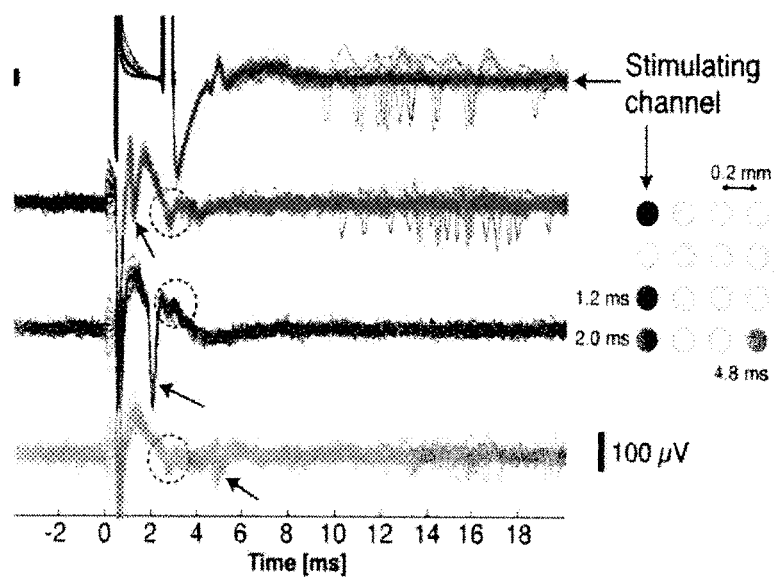

FIGS. 8A-B are graphical illustrations of evoked electrophysiological data recorded from microelectrodes within an individual culture well. In this example, microelectrodes were used to both stimulate and record from neural cortical cultures. In a multiwell format, such data is collected simultaneously in dozens to hundreds of wells, dramatically increasing the throughput of electrophysiological investigations for screening applications. Extracellular electrophysiological data from excitable cells and tissues is used to perform a wide range of analyses, ranging from the collection network-level dose response curves and the identification of specific ion-channel behaviors to the quantification of neurotransmitter release. Additionally, studies in plasticity, toxicity, learning and memory, and pharmacology are further enabled with the use of MEAs. An individual microelectrode can be used to perform multiple functions simultaneously, thus it is possible to both stimulate and record from individual microelectrodes. Stimulation can be used to evoke electrical activity that would other-wise not occur under normal spontaneous conditions. In FIG. 8A, (a) cultured cortical recordings with (b) and without (a) the elimination of excess charge that builds up on the microelectrode during stimulation (known as artifacts) (scale bars: 100 µV, 10 ms, stimulus±0.5V). In FIG. 8B, neural recordings on both the stimulating and neighboring electrodes. Arrows indicate superimposed evoked responses, and circles indicate secondary artifacts induced by crosstalk inside the recording electronics (biphasic stimulus±0.5V).

Without being limited by theory, it is believed that the devices provided herein allow for the measurement of characteristics (eg, chemical, biological, biochemical or electrophysiological) of certain samples (eg, chemical or biological) at sensitivities and/or throughput levels that cannot be achieved with currently available devices.

Accordingly, provided herein are microelectrode arrays (MEAs) which are compatible with equipment or machinery intended for use with an ANSI/SBS-compliant plate, comprising a plate having one or more wells and a substrate comprising a printed circuit board (PCB), wherein said substrate further comprises one or more microelectrodes having a diameter of about 1 to about 500 microns, wherein the substrate is transparent in the vicinity of the microelectrodes and has an area of about 3 inches by about 3 inches or greater. Currently available multiwell MEA plates are restricted to electrodes that are several mm in dimension, precluding the ability to perform electrophysiological measurements, micro-stimulation, or high-resolution impedance analysis.

In certain embodiments, the plate is comprised of a transparent material, such as glass or plastic.

In certain embodiments, the plate comprises a single well.

In certain embodiments, the plate is a multiwell plate. In particular embodiments, the multiwell plate has an area of about 3 inches by about 3 inches or greater. In other embodiments, the multiwell plate has an area of about 3 inches by about 5 inches or greater, about 3 inches by about 6 inches or greater, about 4 inches by about 4 inches or greater, about 4 inches by about 5 inches or greater, about 5 inches by about 5 inches or greater, about 5 inches by about 7 inches or greater or about 6 inches by about 6 inches or greater.

In certain embodiments, the microelectrode array comprises multilayer microelectrode wiring.

In certain embodiments, the microelectrodes are integrated into one or more wells of the multiwell plate. In certain embodiments, the microelectrodes are adhered to or embedded into the substrate.

In certain embodiments, the substrate is transparent in the vicinity of the microelectrodes, such that biological specimens can by analyzed using the MEA in combination with inverted microscopy, inverted fluorescent microscopy, inverted environmental microscopy or inverted cell counting techniques. In certain embodiment, the entire substrate is transparent. In one embodiment, the wells of the multiwell plate are transparent. In another embodiment, the area of the plate in which the microelectrodes are integrated into or attached to is transparent. In particular embodiments, the substrate or plate is transparent such that it allows for about 90%, about 92%, about 94%, about 96%, about 98%, about 99%, about 99.9% light transmittance through the substrate In one embodiment, one or more microelectrodes is itself transparent. Transparency can be measured by methods known to one skilled in the art using a spectrophotometer.

In certain embodiments, the microelectrode array comprises a multiwell plate having anywhere from 4 to 1536 wells, 4 to 384 wells or 4 to 96 wells. In specific embodiments, the multiwell microelectrode array comprises a multiwell plate having 4, 96, 384 or 1536 wells.

In certain embodiments, the multiwell plate is of a size described by ANSI/SBS (ie, is ANSI-SBS-compliant). In certain embodiments, the multiwell plate is compatible with equipment or machinery intended for use with ANSI/SBS-compliant plates. Because it is possible that plate size could be altered without significantly affecting the utility of a microelectrode array, devices including a plate with a size outside of ANSI/SBS standards are intended to be within the scope of the present disclosure.

In certain embodiments, the multiwell plate comprises from 1 to 768 or from 1 to 384 electrodes per well.

In certain embodiments, the multiwell plate comprises 384 electrodes per well in a 2 well configuration to 1 electrode per well in a 1536 well configuration.

In certain embodiments, the multiwell plate has a length of about 127.76 mm±0.25 mm (5.0299 inches±0.0098 inches), a width of about 85.48 mm±0.25 mm (3.3654 inches±0.0098 inches) and a thickness of about 14.35 mm±0.25 mm (0.5650 inches±0.0098 inches).

In certain embodiments, the diameter of the microelectrodes is about 1 to about 500 microns, about 1 to about 450 microns, about 1 to about 400 microns, about 1 to about 350 microns, about 1 to about 300 microns, about 10 to about 300 microns, about 50 to about 300 microns or about 100 to about 200 microns.

In certain embodiments, the microelectrodes have a length of about 1 to about 500 microns, about 1 to about 450 microns, about 1 to about 400 microns, about 1 to about 350 microns, about 1 to about 300 microns, about 10 to about 300 microns, about 50 to about 300 microns or about 100 to about 200 microns.

In certain embodiments, the microelectrodes have a thickness of about 10 nanometers to 1 micron, about 50 nanometers to about 1 micron, about 100 nanometers to about 1 micron, about 200 nanometers to about 1 micron, about 300 nanometers to about 1 micron, about 400 nanometers to about 1 micron, about 500 nanometers to about 1 micron or about 750 nanometers to about 1 micron.

In certain embodiments, neighboring microelectrodes have a spacing of about 10 microns to about 1 mm, about 20 microns to about 1 mm, about 50 microns to about 1 mm, about 100 microns to about 1 mm, about 200 microns to about 1 mm, about 300 microns to about 1 mm, about 400 microns to about 1 mm, about 500 microns to about 1 mm or about 750 microns to about 1 mm.

In certain embodiments, the are made of titanium, chromium, titanium/gold, chromium/gold, platinum, indium tin oxide, rhodium, silver, palladium, nickel, copper, poly(3,4-dioctyloxythiophene) (p-dot) or a combination thereof.

In certain embodiments, the PCB is laminated with a transparent polymer membrane. In certain embodiments, the polymer is Polyethylene Terephthalate (PET). In certain embodiments, the polymer membrane has a thickness of about 10 to about 100 microns).

In certain embodiments, the microelectrode arrays allow for the analysis of 4 to 1536 samples/experiment, 4 to 384 samples/experiment or 4 to 96 samples/experiment.

In certain embodiments, the microelectrode arrays allow for high-sensitivity and high spatial resolution impedance-based assays. Additionally, the use of multiple microelectrodes for impedance analysis provides redundancy, by improving the likelihood that cultures or tissues will adequately cover several electrodes, which may dramatically improve the yield and accuracy of impedance-based assays.

In certain embodiments, the microelectrode arrays allow for micro-stimulation, for eliciting controlled, evoked responses from tissues and cultures under investigation. Such stimulation can be applied simultaneously during the recording and acquisition of extracellular electrophysiological data. Further, micro-stimulation can be used to evoke both field and action potentials as well as to perform a wide-range of threshold-based assays. Accordingly, such methods for using the microelectrode arrays disclosed herein are provided herein.

In certain embodiments, the microelectrode arrays allow for concurrent access to both single-cell and network-level activity of a sample. In certain embodiments, the microelectrode arrays allow for the detection and/or monitoring of electrically active cellular networks. Accordingly, such methods for using the microelectrode arrays disclosed herein are provided herein.

In certain embodiments, the total number of microelectrodes in an array is from 1 to 1536, from 1 to 768, from 1 to 384 or from 1 to 96. In other embodiments, the total number of microelectrodes in an array is a multiple of 96, 384, 786 or 1536, such as a multiple of a whole number between 1 and 5000, between 1 and 4000, between 1 and 3000, between 1 and 2000, between 1 and 1000, between 1 and 500, between 1 and 100, between 1 and 50 or between 1 and 10.

Further provided herein are methods for measuring in vitro or in vivo electrophysiological activity, impedance characteristics, extracellular network activity of a biological specimen (eg, a cell, tissue and/or culture of the following varieties: vertebrate and invertebrate neural, muscle fibers, cardiac, pancreatic islet, osteoblasts, osteoclasts) using a microelectrode array provided herein. Specifically, provided herein are methods for measuring in vitro or in vivo electrophysiological activity, impedance characteristics or extracellular network activity of a cell or tissue, comprising contacting said cell or tissue with a MEA provided herein. In certain embodiments, the biological specimen is placed or cultured in one or more wells of an MEA provided herein and electrophysiological activity, impedance characteristics or extracellular network activity of the biological sample is detected and/or measured.

Further provided herein are methods for microscopy and/or cell counting using a microelectrode array provided herein. In particular embodiments, the microelectrode arrays provided herein are compatible with an optical plate reader.

Further provided herein are methods for in vitro or in vivo micro-stimulation of a biological specimen (eg, a cell, tissue and/or culture of the following varieties: vertebrate and invertebrate neural, muscle fibers, cardiac, pancreatic islet, osteoblasts, osteoclasts). In certain embodiments, provided herein are methods for eliciting controlled, evoked responses from a biological specimen. Such stimulation can be applied simultaneously during the recording and acquisition of extracellular electrophysiological data. Further provided herein are methods for micro-stimulation of a biological specimen and measuring (including recording and/or acquiring) a response (eg, an extracellular electrophysiological response). Further, micro-stimulation can be used to evoke both field and action potentials as well as to perform a wide-range of threshold-based assays. Accordingly, such methods for using the microelectrode arrays disclosed herein are provided herein. Specifically, provided herein are methods for micro-stimulating a cell or tissue comprising contacting said cell or tissue with a MEA provided herein and exposing said cell or tissue to an electrical current originating from said MEA. In another embodiment, such methods further comprise recording and/or acquiring extracellular electrophysiological data from said cell or tissue. In certain embodiments, the biological specimen is placed or cultured in one or more wells of an MEA provided herein and the biological specimen is micro-stimulated by the MEA (eg, by exposing the biological specimen to an electrical current originating from the MEA). Further provided herein are methods for manufacturing a microelectrode array provided herein.

Post Processing Method

Provided herein are methods for manufacturing a microelectrode array including the steps of:
1. providing a PCB and a mask for microelectromechanical systems (MEMS) post processing (wherein in certain embodiments, the PCB is a flex-rigid PCB, and in other embodiments, the PCB and mask are designed to be compatible with an ANSI/SBS-compliant plate);
2. laminating the PCB with a transparent polymer membrane (wherein in certain embodiments, the PCB is a flex-rigid PCB fabricated using a modified process for lamination of PET as described herein);
3. defining vias in the polymer membrane (in certain embodiments, such that it becomes possible to create functional, electrical interconnections between the topside of the polymer membrane, such as PET, and the underlying PCB); and
4. MEMS processing utilizing the PCB as a substrate to create microelectrodes (such as in a multiwell fashion). In certain embodiments, the first layer defines the metal traces on the flex-rigid board and the second layer defines the insulation on top of the defined metal.

Flip-Chip Method

Further provided herein are methods for manufacturing a microelectrode array including the steps of:
1. Defining or modifying a PCB (such as a standard rigid PCB) to allow for insertion of a multiwell glass plate;
2. providing a photolithography mask for processing a multiwell glass MEA (such as a mask designed to be compatible with an ANSI/SBS-compliant multiwell glass plate);

3. optionally fabricating the PCB utilizing standard commercial techniques;
4. microfabricating the multiwell glass MEA to provide at least two layers, wherein the first (bottom) layer defines metal traces and the second (top) layer defines the insulation; and
5. attaching the multiwell glass MEA to the PCB utilizing integrated circuit (IC) packaging techniques, creating electrical connections between the PCB and glass MEA.

In exemplary embodiments, the disclosed fabrication techniques, devices and methods of use may comprise at least one of the following elements:

i. The device: a multiwell MEA device itself, may be any multiwell plate (more than 4 wells) with greater than 4 electrodes per well, with electrode sizes of 500 µm or less in diameter, with inter-electrode distances (center-to-center) of about 1 mm or less. Currently available multiwell MEA devices do not have the capability to define electrodes to the size disclosed in this invention.

ii. The fabrication process: fabricating micro-scale electrodes on printed circuit board (PCB), Kapton flex board, hybrid circuit board technology, flip chip techniques, multi- or single-layer glass technology (i.e. Micronit Inc). More specifically, using printed circuit boards (of any kind) or multilayer glass technology with vias as a substrate for single-well or multiwell MEAs. PCB substrate materials may include, but are not limited to, the following: FR-4, FR-2, Kapton, Polyimide, and Teflon, and Polyethylene Terephthalate (PET). Currently available multiwell MEA devices in large-area ANSI/SBS compliant formats do not utilize microfabrication technologies.

iii. Transparency: in most cell culture applications it is desirable to evaluate or observe the culture with an inverted microscope. Thus, bottom-side transparency, the ability to see through the bottom of the device to observe the underside of the cells, is a desired feature. Laminatable, translucent films such as Kapton and transparent films such as PET (among others) pressed over a hole in the package/PCB substrate to enable inverted microscopy. Such thin films can provide superior optical characteristics like a high degree of light transmittance through the substrate. Glass substrates provide this advantage as well due to light transmission through the substrate. Current multiwell configurations do not disclose this feature.

iv. Applications: using the multiwell MEA as a high throughput instrument for the investigation of electrically active tissue (including, but not limited to, neural and cardiac cells, cellular networks and tissue, spinal cultures and tissue, and muscle tissue), which may have specific applications in drug discovery, basic science, epilepsy research, biosensing, high throughput network or tissue analysis.

v. Connectivity: the use of a PCB or glass substrate as a biochip packaging element and sensor substrate provides an avenue to create bottom side electrical contact pads for 'outside-world' connections or sockets. Bottom side connectivity is made affordable because of via processing readily available in standard PCB and glass-via processes. Additionally, bottom-side connector pads significantly reduce the size of the sensor array, as the connector/socket pads are now on a different plane than the electrodes and can lie directly under the sensor array (outside the transparency region, if applicable). Bottom side metal patterning also creates an opportunity to create a metal heater surface just below the cell culture.

EXAMPLES

A fully microfabricated, packaged and assembled multiwell MEA is shown in FIG. 1 (right hand side). The components of this system include a microfabricated MEA that is constructed utilizing techniques described herein, such as a flip chip package including a glass die with a printed circuit board or a post processed PET-based PCB. This multiwell MEA docks into a system that consists of electronics and signal processing units plus data management/software analysis functionalities.

Biological assays have been conducted using these MEAs to evaluate neuronal cytocompatibility. The various steps for these experiments are described below.

1. To remove potential leachants from microfabrication, the devices were sequentially rinsed in sterile ethanol for 5 minutes, followed by rinsing in sterile DI water for 5 minutes. The multiwell MEAs were then soaked in sterile DI water for up to 72 hours (with a change in DI water every 24 hours). The DI water was then discarded and the MEAs were subjected to a rinse with sterile ethanol. This was followed by an 8 hour dehydration bake at 60° C. in an oven. This bake completed the steps for removing potential leachants from microfabrication and PCB manufacturing.

2. Before plating cells, the MEAs were subject to a 1 min oxygen plasma treatment. This process improves the adherence of cells to the MEAs. This was followed by the coating of 50 µg/mL poly-D-lysine for 2 hrs at 37° C. on the MEA surfaces. Neuronal cells from E18 cortices of rats were cultured on the MEAs with a density of $3 \times 10^5$ cells/cm$^2$. Cells were seeded at the appropriate density in 50 µL of neurobasal media directly on to the center of the MEA devices. Cells were allowed to attach for 30 min at 37° C., then an additional 950 µL of neurobasal media was added to the device. Devices with individual lids were placed inside Petri dishes to minimize media evaporation. The devices with cells were studied using optical microscopy at 1 day, 4 days, 7 days and 21 days in-vitro for neurite outgrowth and general health of the culture. Images of the cell cultures were captured. At 28 days in-vitro live/dead assays were performed in accordance with the procedures described by Cullen et al.

FIG. 7 depicts optical and fluorescent microscopy images of cultures of neuronal cells in an individual well at 21 and 28 days in-vitro.

The extracellular electrode activity from cultured neuronal cells is indicated in FIG. 8. This depicts activity from cells after stimulation was performed with and without the elimination of stimulus artifact.

What is claimed is:

1. An electrophysiology culture plate, comprising:
   a substrate having an upper surface and a lower surface comprising printed circuit board (PCB), the substrate defining a plurality of open ports in the PCB, each port extending from the upper surface to the lower surface of the substrate;
   a plurality of light transmissive optical plates, each optical plate being coupled to the substrate in registration with a respective port to define a substantially transparent region for the respective port;
   a plurality of microelectrodes, wherein each microelectrode is mounted on a top surface of a respective optical plate in the substantially transparent region;
   a plurality of conductive traces, each conductive trace extending from a respective microelectrode mounted on the top surface of the optical plate to an electrical contact exposed on the lower surface of the substrate, wherein the electrical contact is configured to interface with external electronics, and wherein the substrate defines a plurality of vias to operatively receive the plurality of conductive traces;

a plurality of culture wells, wherein each culture well defines an interior cavity and an at least partially open bottom surface, and wherein each culture well is mounted thereto the top surface of a respective optical plate, wherein at least one respective microelectrode of the plurality of microelectrodes underlies the at least partially open bottom surface of a respective culture well and is in communication with the interior cavity of the respective culture well of the plurality of culture wells.

2. The electrophysiology culture plate of claim 1, wherein each optical plate is coupled to the upper surface of the substrate.

3. The electrophysiology culture plate of claim 1, wherein each optical plate is coupled to the lower surface of the substrate.

4. The electrophysiology culture plate of claim 1, wherein each optical plate is coupled to a portion of a respective port defined in the PCB.

5. The electrophysiology culture plate of claim 1, wherein the substantially transparent region of each optical plate is about 96% light transmissive.

6. The electrophysiology culture plate of claim 1, wherein the substantially transparent region of each optical plate is about 99% light transmissive.

7. The electrophysiology culture plate of claim 1, wherein the optical plate is coupled to the substrate by an adhesive layer.

8. The electrophysiology culture plate of claim 1, wherein the optical plate comprises glass.

9. The electrophysiology culture plate of claim 1, wherein the optical plate comprises plastic.

10. The electrophysiology culture plate of claim 1, wherein the plurality of microelectrodes comprise gold.

11. The electrophysiology culture plate of claim 1, wherein the plurality of microelectrodes comprise platinum.

12. The electrophysiology culture plate of claim 1, wherein a portion of the substrate comprises glass.

13. The electrophysiology culture plate of claim 1, wherein the electrophysiology culture plate has a length of between about 102.76 to about 152.76 mm.

14. The electrophysiology culture plate of claim 13, wherein the electrophysiology culture plate has a width of between about 85.23 to about 85.73 mm.

15. The electrophysiology culture plate of claim 14, wherein the electrophysiology culture plate has a thickness of between about 14.1 to about 14.6 mm.

16. The electrophysiology culture plate of claim 1, wherein at least one of a length, a width, and a thickness of the electrophysiology culture plate conforms to at least one of American National Standards Institute standards and Society for Lab Automation and Screening standards.

17. The electrophysiology culture plate of claim 1, wherein the plurality of electrodes comprises from between about 2 to about 1536 microelectrodes.

18. The electrophysiology culture plate of claim 1, wherein the total number of electrodes in an array is an integer multiple of at least one of 96, 384, 786, and 1536.

19. The electrophysiology culture plate of claim 1, wherein each microelectrode of the plurality of electrodes is configured to both stimulate and record data.

20. The electrophysiology culture plate of claim 19, wherein stimulating further comprises evoking electrical activity in a biologic cell disposed in a culture well.

21. The electrophysiology culture plate of claim 19, wherein recording data further comprises recording data from individual biologic cells disposed in a respective culture well.

22. The electrophysiology culture plate of claim 19, wherein recording data further comprises recording data from cellular networks.

23. A system, comprising:
an electrophysiology culture plate, comprising:
a substrate having an upper surface and a lower surface comprising printed circuit board (PCB), the substrate defining a plurality of open ports in the PCB, each port extending from the upper surface to the lower surface of the substrate;
a plurality of light transmissive optical plates, each optical plate being coupled to the substrate in registration with a respective port to define a substantially transparent region for the respective port;
a plurality of microelectrodes, wherein each microelectrode is mounted on a top surface of a respective optical plate in the substantially transparent region;
a plurality of conductive traces, each conductive trace extending from a respective microelectrode mounted on the top surface of the optical plate to an electrical contact exposed on the lower surface of the substrate, wherein the electrical contact is configured to interface with external electronics, and wherein the substrate defines a plurality of vias to operatively receive the plurality of conductive traces;
a plurality of culture wells, wherein each culture well defines an interior cavity and an at least partially open bottom surface, and wherein each culture well is mounted thereto the top surface of a respective optical plate,
wherein at least one respective microelectrode of the plurality of microelectrodes underlies the at least partially open bottom surface of a respective culture well and is in communication with the interior cavity of the respective culture well of the plurality of culture wells;
at least one physical system positioned in the interior cavity of at least one of the plurality of culture wells on the culture plate; and
a signal processing and data management system configured to stimulate the at least one physical system and amplify and process raw data received from the at least one physical system via the electrical contact.

24. The system of claim 23, wherein the optical plate is coupled to the substrate by an adhesive layer.

25. The system of claim 23, wherein the optical plate comprises glass.

26. The system of claim 23, wherein the optical plate comprises plastic.

27. The system of claim 23, wherein the plurality of microelectrodes comprise gold.

28. The system of claim 23, wherein the plurality of microelectrodes comprise platinum.

29. The system of claim 23, wherein a portion of the substrate comprises glass.

30. The system of claim 23, wherein the electrophysiology culture plate has a length of between about 102.76 to about 152.76 mm.

31. The system of claim 23, wherein the electrophysiology culture plate has a width of between about 85.23 to about 85.73 mm.

32. The system of claim 23, wherein the electrophysiology culture plate has a thickness of between about 14.1 to about 14.6 mm.

33. The system of claim 23, wherein at least one of a length, a width, and a thickness of the electrophysiology culture plate conforms to at least one of American National Standards Institute standards and Society for Lab Automation and Screening standards.

34. The system of claim 23, wherein the plurality of electrodes comprises from between about 2 to about 1536 microelectrodes.

35. The system of claim 23, wherein the total number of electrodes in an array is an integer multiple of at least one of 96, 384, 786, and 1536.

36. The system of claim 23, wherein each microelectrode of the plurality of electrodes is configured to both stimulate and record data.

37. The system of claim 36, wherein stimulating further comprises evoking electrical activity in a biologic cell disposed in a culture well.

38. The system of claim 36, wherein recording data further comprises recording data from individual biologic cells disposed in a culture well.

39. The system of claim 36, wherein recording data further comprises recording data from cellular networks.

40. The system of claim 23, wherein each optical plate is coupled to the upper surface of the substrate.

41. The system of claim 23, wherein each optical plate is coupled to the lower surface of the substrate.

42. The system of claim 23, wherein each optical plate is coupled to a portion of a respective port defined in the PCB.

43. The system of claim 23, wherein the substantially transparent region of each optical plate is about 96% light transmissive.

44. The system of claim 23, wherein the substantially transparent region of each optical plate is about 99% light transmissive.

* * * * *